(12) United States Patent
McSweeney et al.

(10) Patent No.: US 11,871,182 B2
(45) Date of Patent: Jan. 9, 2024

(54) SOUND PROCESSORS

(71) Applicant: Hemideina Pty Ltd, East Melbourne (AU)

(72) Inventors: Toby McSweeney, East Melbourne (AU); Kathryn Lomas, East Melbourne (AU)

(73) Assignee: Hemideina Pty Ltd, East Melbourne (AU)

( * ) Notice: Subject to any disclaimer, the term of this patent is extended or adjusted under 35 U.S.C. 154(b) by 0 days.

(21) Appl. No.: 17/774,061

(22) PCT Filed: Jul. 6, 2021

(86) PCT No.: PCT/AU2021/050719
§ 371 (c)(1),
(2) Date: May 3, 2022

(87) PCT Pub. No.: WO2022/006625
PCT Pub. Date: Jan. 13, 2022

(65) Prior Publication Data
US 2022/0377472 A1 Nov. 24, 2022

(30) Foreign Application Priority Data

Jul. 6, 2020 (AU) ................................ 2020902322
Jul. 30, 2020 (AU) ................................ 2020902670

(51) Int. Cl.
*H04R 25/00* (2006.01)
*A61N 1/36* (2006.01)
(Continued)

(52) U.S. Cl.
CPC .......... *H04R 25/505* (2013.01); *A61N 1/025* (2013.01); *A61N 1/0541* (2013.01);
(Continued)

(58) Field of Classification Search
CPC .. A61N 1/025; A61N 1/0541; A61N 1/36038; A61N 1/36128; A61N 1/37229;
(Continued)

(56) References Cited

U.S. PATENT DOCUMENTS 10,341,787 B2   7/2019  Blum et al.
2006/0287690 A1  12/2006  Bouchataoui et al.
(Continued)

FOREIGN PATENT DOCUMENTS

WO   WO 2020/142812 A1   7/2020
WO   WO-2021054940 A1 * 3/2021 ........... A61N 1/0541

*Primary Examiner* — Phylesha Dabney
(74) *Attorney, Agent, or Firm* — Blank Rome LLP

(57) ABSTRACT

A sound processor comprises one or more electrical signal outputs configured to generate a plurality of electrical signals. The plurality of electrical signals are generated in specific tuned audio frequency bands in respective audio channels, in response to sound information received at the sound processor in the specific tuned audio frequency bands. The sound processor further comprises a transmitter coupled to the one or more electrical signal outputs for transmission of the plurality of electrical signals. The transmitter is configured to transmit the electrical signal in the respective audio channel over a separate respective transcutaneous communication link.

25 Claims, 9 Drawing Sheets

(51) Int. Cl.
*A61N 1/02* (2006.01)
*A61N 1/05* (2006.01)
*A61N 1/372* (2006.01)
*A61N 1/378* (2006.01)

(52) U.S. Cl.
CPC ..... *A61N 1/36038* (2017.08); *A61N 1/36128* (2013.01); *A61N 1/3787* (2013.01); *A61N 1/37229* (2013.01); *H04R 25/554* (2013.01); *H04R 25/606* (2013.01); *H04R 2225/025* (2013.01); *H04R 2225/67* (2013.01)

(58) Field of Classification Search
CPC .............. A61N 1/3787; A61N 1/37223; H04R 2225/025; H04R 2225/67; H04R 25/505; H04R 25/554; H04R 25/606; H04R 17/10; H04R 2410/03; H04R 2430/03; H04R 2460/13

USPC ......................................................... 381/312
See application file for complete search history.

(56) References Cited

U.S. PATENT DOCUMENTS

| | | |
|---|---|---|
| 2013/0103111 A1 | 4/2013 | Meskens |
| 2016/0199641 A1 | 7/2016 | Arweiler |
| 2018/0071541 A1 | 3/2018 | Meskens |
| 2018/0272131 A1 | 9/2018 | Meskens |
| 2021/0321207 A1* | 10/2021 | Lomas ................. H04R 25/554 |

* cited by examiner

SOUND PROCESSORS

CROSS-REFERENCE TO RELATED APPLICATIONS

This application is a national stage filing of PCT Application No. PCT/AU2021/050719, filed Jul. 6, 2021, which claims priority to Australian Patent Application No. 2020902670, filed Jul. 30, 0202, and also claims priority to Australian Patent Application No. 2020902322, filed Jul. 6, 2020, each of which are hereby incorporated by reference in their entirety.

TECHNICAL FIELD

The present disclosure relates to sound processors such as microphones, in particular in-ear sound processors for cochlear implants and other implantable hearing devices. It further relates to a system, a medical implant and a method.

BACKGROUND

A cochlear implant is a surgically implanted neuroprosthetic device that provides a sense of sound to a person with severe to profound sensorineural hearing loss. Current cochlear, bone conduction and hearing implants have both implanted components and external components, including microphones, sound processing electronics and a battery. The implants require power levels that can utilise either external power delivery via a transcutaneous link or an internal battery. Conventional cochlear implants and other implantable hearing devices send data and power across a single RF (inductive) link. This can result in sub-optimal power delivery to the implant when data is also transferred over the link. Cochlear implants break down sound information into discrete frequency bands and then transfer the data packets, which are required to be delivered to multiple sites inside the cochlear to recreate speech. The discretisation of the data can add delay in the data transfer. Furthermore, as sound coding strategies for use with cochlear implants have generally been optimised for speech recognition, low frequency information known as the temporal fine structure (TFS) that is naturally used by the auditory system for binaural cues for sound and noise isolation and directionality, is removed or filtered out. Clinical evidence has indicated that the TFS is also important for the understanding of melody and pitch in sound.

It is desired to address or ameliorate one or more shortcomings of conventional cochlear implant technology, or to at least provide a useful alternative thereto.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Embodiments of the disclosure provide a sound processor that includes a communications arrangement configured to transmit multiple audio data signals across separate transcutaneous communications links to a receiver-stimulator of a cochlear implant. The arrangement aims to preserve the low frequency data in sound signals received at the sound processor as it is transmitted to the implant.

According to a first aspect, a sound processor comprises one or more electrical signal outputs configured to generate a plurality of electrical signals, wherein the plurality of electrical signals are generated in specific tuned audio frequency bands in respective audio channels, in response to sound information received at the sound processor in the specific tuned audio frequency bands, and further comprising a transmitter coupled to the one or more electrical signal outputs for transmission of the plurality of electrical signals, wherein the transmitter is configured to transmit the electrical signal in the respective audio channel over a separate respective transcutaneous communication link.

The sound processor generates a plurality of electrical signals, each corresponding to a particular frequency band, and each signal being transmittable over a separate transcutaneous communication link, rather than a single signal covering all frequencies being transmitted over a single communications link. This arrangement allows low frequency electrical signals containing the TFS information to be transmitted across separate communications links in addition to separate transmission of higher frequency electrical signals, without filtering or discarding of audio information. As a result, the user experience is enriched when trying to understand speech in noisy environments and also provides a greater richness of sound through the retention of the TFS information.

In some embodiments, the transmitter may comprise a plurality of interfaces, each of the interfaces coupled to a respective one of the plurality of electrical signal outputs, each of the interfaces configured to transmit a respective one of the electrical signals over one of the separate respective transcutaneous communication links. The plurality of interfaces may be wireless interfaces or they may each comprise a wire.

In some embodiments, the sound processor comprises a further plurality of electrical signal outputs tuned to specific audio frequency bands in respective audio channels and each configured to generate an electrical signal based on sound information received at the sound processor in each respective tuned audio frequency band, the transmitter configured to transmit each of the electrical signals generated at the further plurality of electrical signal outputs over a single transcutaneous communication link. The transmitter may comprise a further interface, the further interface coupled to the further plurality of electrical signal outputs and configured to transmit the electrical signals generated at the further plurality of electrical signal outputs over the single transcutaneous communication link.

In some embodiments, the one or more electrical signal outputs and the further plurality of electrical signal outputs may be directly connected to the plurality of interfaces and the further interface.

The plurality of interfaces and the further interface may be passive, i.e. they do not require any active electronics to perform their function. Each of the wireless interfaces may comprise an inductive coil, for example a planar inductive coil or solenoid coil. Each respective inductive coil may be tuned to its corresponding electrical signal output so that the natural oscillation frequency of the electrical signals generated at the sound processor can drive the coil directly and thus transfer its acoustic information without disconnect or break in the signal chain. Accordingly, the acoustic information can be transferred, e.g. to a hearing device such as a cochlear implant, without delay.

Each interface of the plurality of interfaces is tuned to an audio signal frequency.

In some embodiments, the sound processor is a small device that may be sized to fit in the ear canal of a patient. There is therefore a need to minimise transmission interference between the separate transcutaneous communication links. In some embodiments, at least a portion of the interfaces of the plurality of interfaces are tuned to a natural frequency of an electrical signal output by a respective electrical signal of output to which they are coupled. At least one interface of the plurality of interfaces may be tuned to a carrier frequency selected to reduce cross-coupling across the transcutaneous communication links. In this arrangement, the electrical signal is carried at the carrier frequency to avoid interference during transmission with the transmission of another of the electrical signals. The natural frequency of the electrical signal can be reseparated from the remainder of the transmitted signal at the carrier frequency once it has been received at the implant.

In some embodiments, the one or more electrical signal outputs comprises a plurality of electrodes. The sound processor may comprise a plurality of resonators, each resonator of the plurality of resonators coupled to a respective electrode of the plurality of electrodes, wherein each of the electrical signals generated at the electrodes is responsive to incident sound at the respective resonator of the plurality of resonators, at least a portion of the plurality of resonators having a different natural frequency. The plurality of resonators may be piezoelectric resonators or strain gauge resonators or capacitive cell resonators.

In some embodiments, the sound processor may further comprise an earbud enclosure for insertion into an ear canal or for mounting on or behind the ear; wherein the plurality of resonators and the transmitter are provided within the earbud enclosure. In some embodiments, the transmitter is provided externally of an earbud enclosure enclosing the sound processor and the transmitter is attached to the sound processor via a cable.

According to another aspect of the disclosure, there is provided a system comprising the sound processor of the first aspect; and an implant comprising: a plurality of implant electrodes, each implant electrode configured to stimulate a neuron of the cochlea; a receiver-stimulator configured to: receive, over separate transcutaneous communication links, each of the electrical signals transmitted from the transmitter, and apply each of the electrical signals to a respective one of the plurality of implant electrodes. In some embodiments, the transmitter is a wireless transmitter and the receiver-stimulator is a wireless receiver-stimulator.

In some embodiments, the electrical signals transmitted from the transmitter include electrical signals generated at the one or more electrical signal outputs and electrical signals generated at the further plurality of electrical signal outputs.

In some embodiments, the receiver-stimulator may comprise a plurality of voltage controlled current sources or, alternatively, a plurality of charge pumps or voltage doublers, each voltage controlled current source or charge pump or voltage doubler configured to apply charge to a respective one of the plurality of electrical signals generated by the plurality of electrical signal outputs being applied to the plurality of implant electrodes. Accordingly, the amplitude of each of the electrical signals can be boosted to a level sufficient to stimulate the respective one of the plurality of implant electrodes.

In some embodiments, the implant may further comprise a power source. The power source may be rechargeable via the wireless receiver over a separate transcutaneous communication link, for example via a separate inductive link. In this arrangement, the sound data and the power are transferred over separate transcutaneous communication links so that optimum power can be provided to the implant whilst avoiding delay in the transfer of the sound data. Alternatively, the implant may be powered by an external power source via a separate wireless communication link or wire.

In some embodiments, the sound processor is enclosed in an earbud, and wherein the wireless receiver-stimulator is configured to align with the wireless transmitter when the implant is implanted near or adjacent to an ear or ear canal of a patient and the earbud is inserted into the ear.

The earbud may comprise one or more keying features configured to engage with one or more features of an ear to locate the wireless transmitter in a predetermined orientation relative to the ear when the earbud is inserted into the ear. According to this arrangement, magnets are not required to locate wireless interfaces of the in-ear sound processor in position, as is the requirement with some conventional cochlear implants.

According to another aspect of the disclosure, there is provided a medical implant comprising: a plurality of implant electrodes, each implant electrode configured to stimulate a neuron of the cochlea; a receiver-stimulator configured to: receive, over separate transcutaneous communication links, a plurality of electrical signals transmitted from a transmitter of an in-ear, on-ear or behind the ear sound processor; and apply each of the electrical signals to a respective one of the plurality of implant electrodes.

The sound processor may be the sound processor of the first aspect of the disclosure.

The medical implant may be configured to apply each of the electrical signals to a respective one of the electrodes simultaneously. The medical implant may be configured to apply each of the electrical signals to a respective one of the electrodes sequentially.

According to a still further aspect of the disclosure, there is provided a method, comprising: generating an electrical signal responsive to sound incident at a piezo-electric resonator of a plurality of piezo-electric resonators; and applying the electrical signal to an electrode proximate a neuron of the cochlear, wherein a frequency of the electrical signal is within a phase-locking frequency range of the neuron.

The method may comprise generating a plurality of the electrical signals, each electrical signal responsive to sound incident at one of a plurality of the resonators; and applying each electrical signal to a separate electrode, each separate electrode proximate a different neuron of the cochlea; wherein a frequency of each of the electrical signals is within a phase-locking frequency range of the neuron of the cochlea to which it is proximate. The method may apply each of the electrical signals to a respective one of the electrodes simultaneously or sequentially.

BRIEF DESCRIPTION OF DRAWINGS

Embodiments of the disclosure will now be described by way of example only with reference to the accompanying drawings, in which.

DESCRIPTION OF EMBODIMENTS

Embodiments of the present disclosure aim to overcome or at least alleviate difficulties associated with the retention of and transmission of sound information in hearing systems, such as state of the art cochlear hearing systems.

Specifically, embodiments of the present disclosure relate to sound processors that are capable of transducing acoustic sound pressure waves into electrical signals with a reduced requirement for complex sound processing, and of transmitting the electrical signals at audio frequency ranges over separate audio data transcutaneous communication links.

Figure 1:
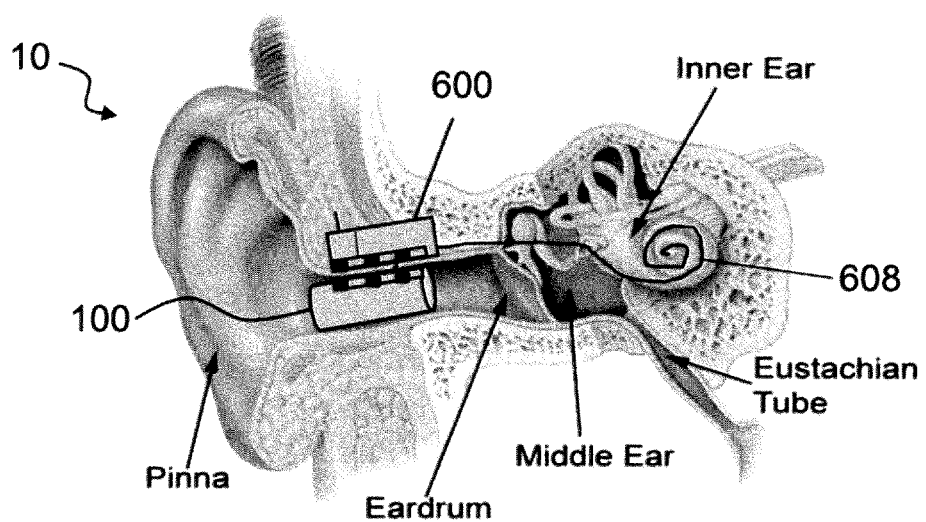
FIG. 1 is an anatomic representation of an earbud including a sound processor and communication link, according to embodiments of the present disclosure, inserted into an ear canal and coupled to a cochlear implant.

FIG. 1 is an anatomic representation of a human ear, and a system 10 in accordance with embodiments of the invention. The system 10 includes a sound processor 100 for transducing sound waves into electrical signals and a medical implant 600, such as a cochlear implant. As shown in FIG. 1, the sound processor 100 is shown inserted in the ear canal of a user. The sound processor 100 has one or more electrical signal outputs, e.g. a single electrical output or a plurality of electrical signal outputs, each tuned to a specific audio frequency band. Each electrical signal output is configured to generate an electrical signal based on sound information received at the sound processor in each respective tuned audio frequency band.

The electrical signals are transmitted to the cochlear implant 600 that is implanted in the ear of the user. The cochlear implant 600 includes a receiver-stimulator comprising a receiver 602 (seen in FIGS. 8-11) for receiving the electrical signals, a processor 606 (seen in FIGS. 8-11) for processing the received electrical signals, and an electrode array 608 (seen in FIGS. 1, 8-12) for stimulating the nerves of the cochlear.

The sound processor 100 may take various forms. In one preferred embodiment, the sound processor 100 is a mechanical sound processor that includes an acoustic device 300. The acoustic device 300 includes a plurality of resonators each configured to generate an electrical signal responsive to incident sound, as will be described herein. Each of the plurality of resonators typically has a different natural frequency and generates an electrical signal at a respective one of the electrical signal outputs. In another embodiment, the sound processor is a conventional digital sound processor in which electrical signals are output from a multi-channel band pass filter. In either embodiment of the sound processor 100, electrical signals are generated at the respective electrical signal outputs based on sound information received at the sound processor. A transmitter is coupled to the one or more electrical signal outputs and is configured to transmit each of the electrical signals over a separate respective transcutaneous communications link. The sound processor 100 may include a further plurality of electrical signal outputs in addition to the one or more electrical signal outputs. For example, the mechanical sound processor may include a further acoustic device 300 providing the further plurality of electrical signal outputs. The transmitter is configured to transmit each of the electrical signals generated at the further plurality of electrical signal outputs over a single transcutaneous communication link.

Figure 2:
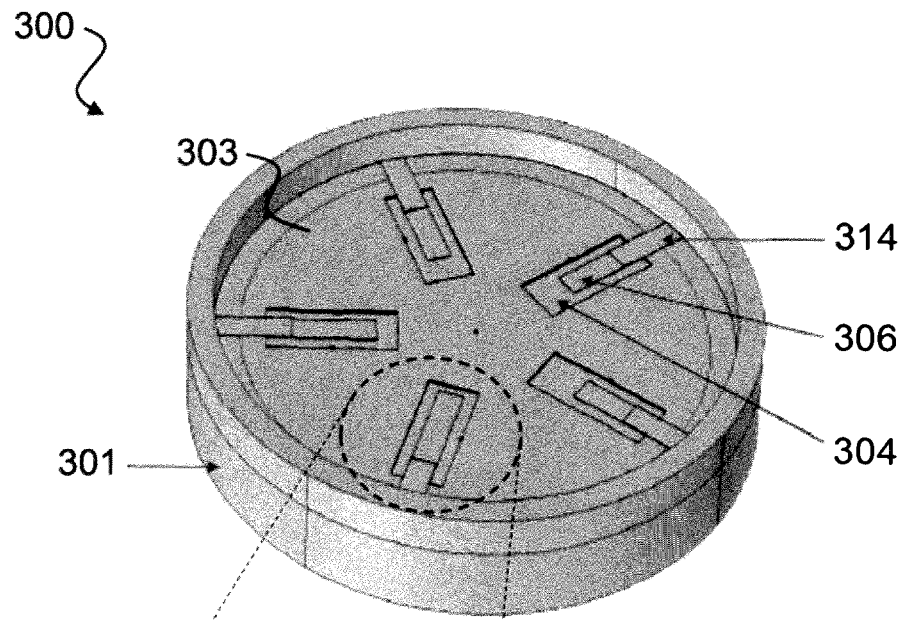
FIG. 2 is a diagram of an acoustic device according to embodiments of the present disclosure.
Figure 3:
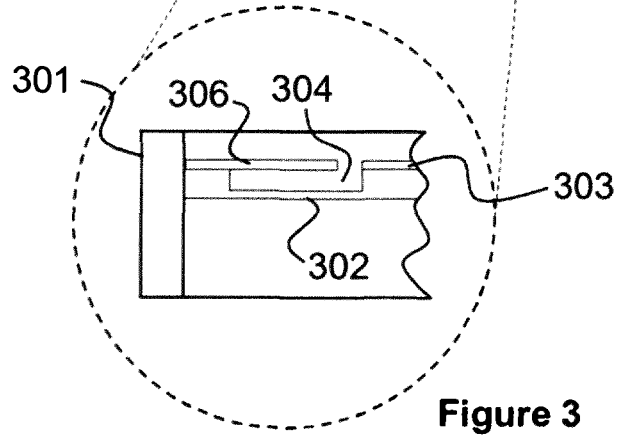
FIG. 3 is a close up cross sectional view of part of the acoustic device shown in FIG. 2.
Figure 4:
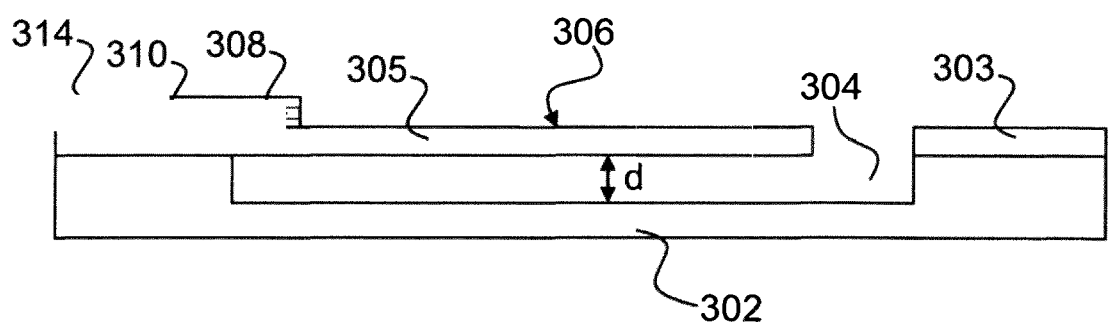
FIG. 4 is a partial cross sectional view of the acoustic device of FIG. 2.

FIGS. 2 to 4 are perspective and side views of includes an acoustic device 300 that can be used in the sound processor 100 to generate the electrical signals according to an embodiment of the present disclosure. The acoustic device 300 is a mechanical sound processor as is described fully in the applicant's published PCT application WO2020/142812, the entirety of which is hereby incorporated by reference. FIG. 3 shows only part of the acoustic device 300 shown in FIG. 2, as denoted by the broken-line circles. FIG. 4 is a more detailed side view of the part of the acoustic device 300 shown in FIG. 7. The device 300 comprises a support ring 301 which supports an acoustic membrane 302 having a plurality of resonator cavities 304 formed therein, and a piezoelectric resonator 306 supported over each of the cavities 304.

In the embodiment shown, the plurality of resonators 306 are integrally formed as part of a resonator layer 303 disposed over the acoustic membrane 302. By providing the resonator layer 303 over the acoustic membrane 302, low frequency sound path differences around the resonator banks are substantially reduced. As such, the acoustic membrane 302 acts as a baffle increasing the sound shadow at the front and rear surfaces of the device 300. The resonator layer 303 and the acoustic membrane 302 may be glued, laminated or otherwise fixed to one another. The acoustic membrane 302 may have a thickness of between 50 and 150 microns. The resonator layer 303 is preferably thinner than the acoustic membrane 302. In some embodiments, the resonator layer 303 may have a thickness of between 10 and 50 microns, for example 25 microns. In some embodiments, the membrane layer 302 may have a thickness of between 50 and 100 microns, for example 75 microns. The ratio of thicknesses of the acoustic membrane 302 to the resonator layer 303 may be in the region of 2.5-3.5:1. In other embodiments, the acoustic membrane 302 and the resonator layer 303 may be made up of a single layer, the plurality of piezoelectric resonators integrated into the acoustic membrane 302.

The acoustic device 300 may have a total radius of between 500 microns and 20 mm. In some embodiments, the radius of the device may be chosen to conform to a human ear canal. In the embodiment shown, the acoustic device 300 is substantially cylindrical in shape. In other embodiments, the acoustic device 300 may be a different shape, for example, oval, square, or rectangular.

A piezoelectric cantilever resonator 306 is supported over each of the resonator cavities 304. In some embodiments, each cantilever resonator 306 is fixed to the support ring 301. Additionally or alternatively, each cantilever resonator 306 is fixed to the acoustic membrane 302, for example, using glue or the like. In the embodiment shown, the resonators 306 are coupled to the acoustic membrane 302 through their integration with the resonator layer 303 which in turn is fixed to the acoustic membrane 302. By integrating the resonators 306 into the resonator layer 303, the bulk of the resonator layer 303 (i.e. the portion of the resonator layer 303 other than the resonators 306) acts as a dampener to prevent cross-talk from a resonating one of the resonators 306 to others of the resonators 306. Since the bulk portion of the resonator layer 303 has a much larger mass than each of the resonators 306, its resonant frequency is outside of the range of resonant frequencies of the resonators 306, thus acting to dampen any potential cross-talk between any of the resonators 306.

Each resonator 306 may have a thickness of between 20 and 30 microns, for example, around 25 microns. For example, each resonator 306 may have the same thickness as the remainder of the resonator layer 303 into which it is integrated. Minimizing the thickness of the resonator 306 reduces the mass of the resonator 306 and thus the amount of sound pressure required to move the resonator 306. Minimizing the thickness of the resonators 306 may also affect their resonant frequency as discussed above.

In some embodiments, the resonator cavity 304 has a depth, d, of between 25 and 100 microns, The effect of providing a relatively large gap between the acoustic membrane 302 and the cantilever resonators 306 is that it allows for greater displacement of the beam resonators 306. The thickness of the membrane 302 below the cavity 304 may be between 20 and 30 microns, for example 25 microns.

Each cantilever beam resonator 306 comprises a free end which is configured to resonate in response to incident sound pressure waves. In the embodiment shown, the cantilever resonators 306 are arranged radially around the acoustic device 300. In some embodiments, the cantilever resonators 306 may have a length between 1 and 4 mm.

Each of the piezoelectric cantilever resonators 306 may comprise a cantilever beam 305. To convert the displacement of the cantilever beam 305 into an electrical signal, each piezoelectric cantilever resonator 306 may further comprise a piezoelectric layer 308, a ground layer 310 and an electrical signal output in the form of an electrode 314. The ground layer 308 may be formed over the cantilever beam 305. The piezoelectric layer 308 may be formed over the ground layer 310. The electrode 314 may be formed over the piezoelectric layer 308. In the embodiment shown, only the cantilever beam 305 is integrated into the resonator layer 303 with the piezoelectric layer 308 and the electrode 314 located on top of the resonator layer 303. In other embodiments one or more of the piezoelectric layer 308, the ground layer 310 and the electrode 314 may be integrated into the resonator layer 303 without departing from the scope of the disclosure.

Each of the electrodes 314 may be provided over the piezoelectric layer 308 to electrically couple each beam resonator 306 to external sensing electronics and/or a transmitter (seen in FIGS. 8 to 11). The piezoelectric layer 308, ground layer 310 and electrodes 314 may be positioned so as not to substantially overlap the resonator cavity 304 or the cantilever resonators 306. Rather, the piezoelectric layer 308, ground layer 310 and electrodes 314 may be positioned at the edges of the device 300 overlapping a portion of the cantilever beam 305. By providing some overlap of the cantilever beam 305 positioned over the acoustic cavity 304, movement of the cantilever beam 305 will cause the piezoelectric layer 308 to generate a charge representative of the acoustic signal presented to the beam resonator 306.

As mentioned above, the electrodes 314 may be coupled to sensing electronics. Sensing electronics may include variable gain amplifiers or operational amplifiers, such as hybrid junction field effect transistor (JFET) operational amplifiers or the like. Sensing circuits may be provided on an application specific integrated circuit (ASIC) or the like which may be coupled to the diaphragm or provided separately. Signal transmission electronics may also be provided with the sensing circuits as will be discussed in more detail below.

The piezoelectric beam resonators 306, cavity 304, membrane 302 and/or electrodes 314 may be formed by additive manufacturing (or three-dimensional (3D) printing). The additive manufacturing may, for example, comprise projection micro stereolithography (or stereo-lithographic printing (SLP) or digital light processing (DLP)). Suitable projection micro stereolithography techniques and materials are described in 3D Optical Printing of Piezoelectric Nanoparticle-Polymer Composite Materials, ACS Nano 8(10), July 2014. In some embodiments, the piezoelectric beam resonators 306, cavity 304, membrane 302 and/or electrodes 314 may be formed by laser cutting sheet (shim) plastic (e.g. polyethylene terephthalate) or metal (e.g. copper or brass) to form one or more layers of the device 300.

The acoustic membrane 302 may be formed from a polymer material, for example, polyethylene glycol diacrylate (PEGDA). The electrodes 314 may be formed from an electrically conductive nanostructure-polymer composite material, for example, a carbon nanotube (CNT)-PEGDA composite material. The piezoelectric layer 308 of the piezoelectric beam resonators 306 may be formed from a piezoelectric nanoparticle-polymer composite material, for example, a barium titanate ($BaTiO_3$, BTO)-PEGDA composite material. Other equivalent conductive and piezoelectric polymer composite materials may also be used. Example materials include $BaTiO_3$, $PbTiO_3$, $Pb(Zr, Ti)O_3$, $Pb(Mg_{1/3}Nb_{2/3})o_3\text{-}PbTiO_3$, and $(Pb0.8725SM0.085)(Ti0.98Mn0.02)O_3$.

During operation, sound pressure waves incident the beam resonators 306 induce motion in the array of beam resonators 306 which causes changes in strain in each of the beam resonators 306. Each beam resonator 306 is configured to resonate at a particular frequency of incident sound pressure waves. When a resonator beam 306 begins to resonate, displacement of the beam 306 towards the acoustic cavity 304 displaces air in the cavity 304 increasing the sound pressure in the cavity 304 below the beam resonator 306. This increase in sound pressure causes the subsequent displacement of the beam resonator 306 away from the acoustic membrane 302 to be substantially larger than it would be in absence of the acoustic membrane 302 (and thus the cavity 304). The inventors have found that the provision of the partially enclosed cavity 304 below the beam resonator 306 can lead to an increase in displacement of a beam resonator 306 of up to 90% or more in some embodiments.

Piezoelectrically transduced signals generated by the piezoelectric layers 308 are then captured by the electrodes 314. The greater the displacement of the resonator beam 305, the greater the voltage produced at the electrode 314.

Since the amplitude of the piezoelectrically transduced signals generated at each cantilever resonator 306 is proportional to the total displacement of the cantilever resonators 306, by providing an array of cantilever resonators 306, a plurality of mechanically frequency selective signals can be output from the acoustic device 300. As such, in contrast to conventional microphones which output an electrical signal pertaining to an entire frequency range of human hearing, e.g. 20 to 10000 Hz, the acoustic device 300 may output a plurality of electrical signals relating to frequency sub-bands of the human hearing frequency range. For example, the sound processor 100 may include two acoustic devices 300a, 300b, having a total of ten cantilever resonators manufactured in accordance with the above, each having a different resonant frequency, the resonant frequencies spanning 200 Hz to 6000 Hz. Frequency ranges can be tuned by adjusting one or more of cantilever length, cantilever width, cantilever thickness, cantilever composition, and cantilever compliance, so that they match the tonotopy of the human cochlea.

The acoustic device 300 described herein may be formed by 3D printing of a plastic material. For configuration as an in-ear or behind ear sound processor such as sound processor 100, one or more components of the acoustic devices described herein may be formed from a soft, bio-compatible, plastic material suitable for being in contact with human skin for extended periods.

Piezoelectric resonators of the various acoustic devices described herein may, for example, be formed from mouldings, laminates and/or films of piezo-polymers, polyvinylidene fluoride (PVDF), and/or piezo-ceramics. Other suitable piezoelectric materials include $BaTiO3$, $PbTiO3$, $Pb(Zr, Ti)O3$, $Pb(Mg1/3Nb2/3)o3\text{-}PbTiO3$, and $(Pb0.8725SM0.085)(Ti0.98Mn0.02)O3$.

Figure 10:
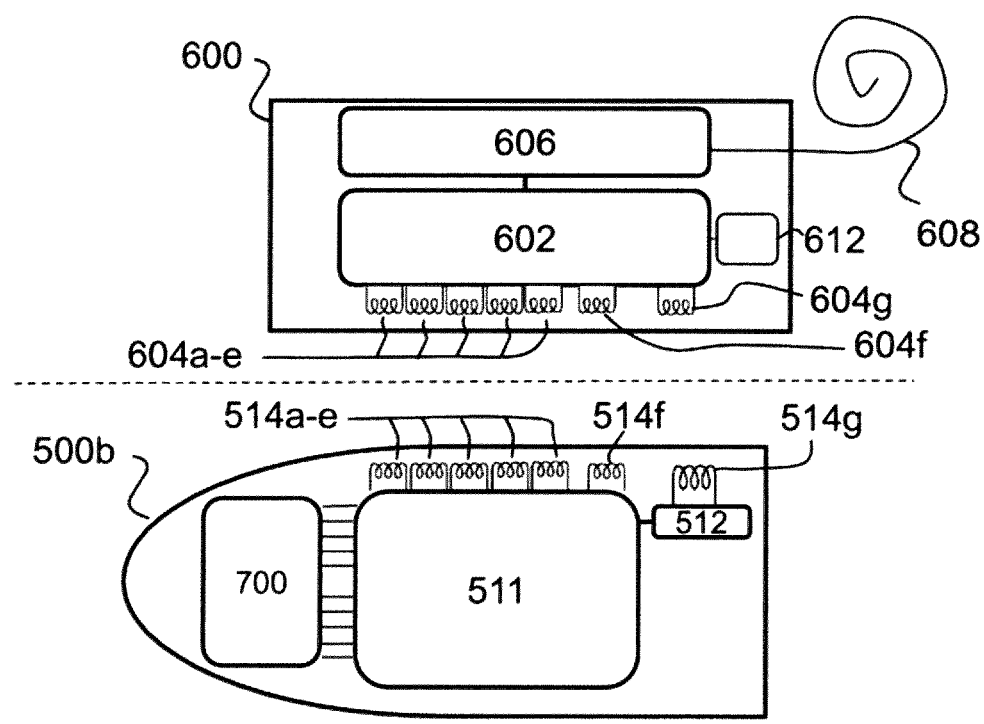
FIG. 10 is a schematic diagram of an earbud enclosing the sound processor and wireless communication links according to a further embodiment of the disclosure and the cochlear implant shown in FIG. 1.
Figure 11:
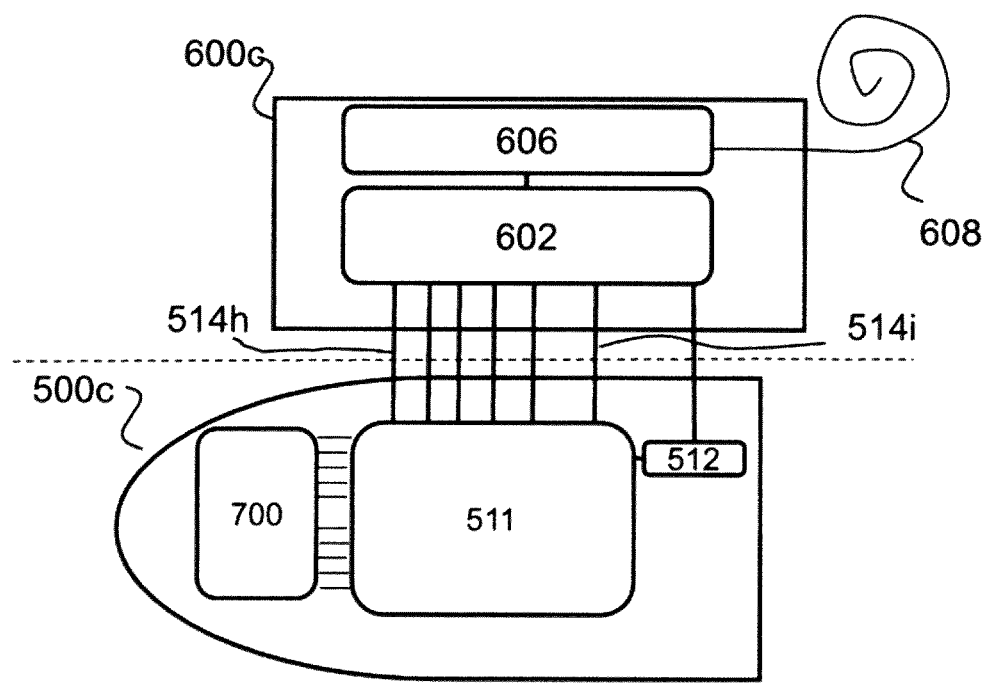
FIG. 11 is a schematic diagram of an earbud enclosing the sound processor and wired communication links according to a further embodiment of the disclosure and the cochlear implant shown in FIG. 1.

In an alternative embodiment of the sound processor 100, the acoustic device 300 is replaced with a conventional microphone 700, shown schematically in FIGS. 10 and 11. The conventional microphone 700 transduces received sound information into electrical signals and outputs the electrical signals at a multi-channel band pass filter. The multi-channel band pass filter as electrical signal output may output a plurality of electrical signals in specific tuned audio frequency bands in separate audio channels for transmission to the implant 600.

Figure 5:
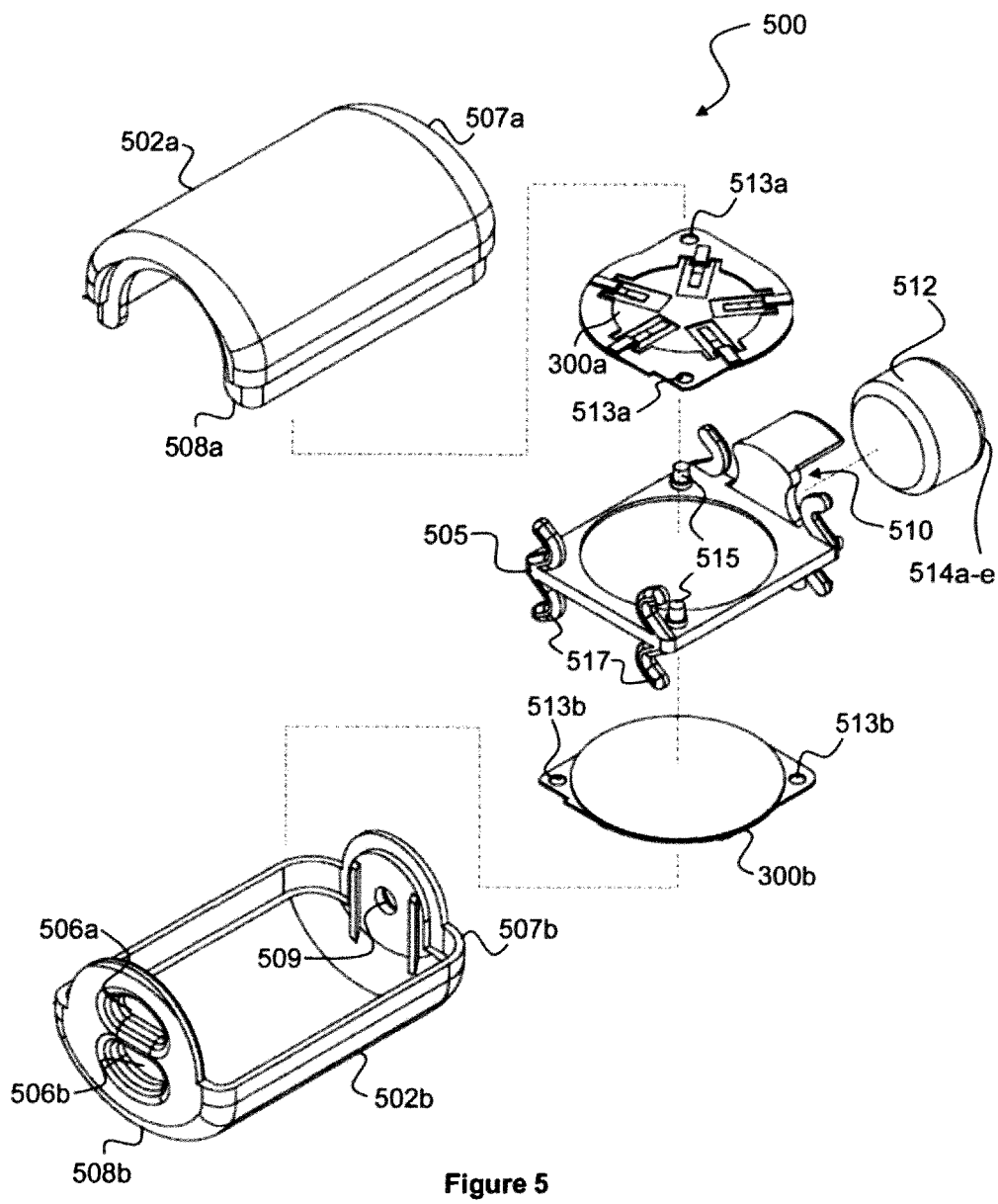
FIG. 5 is an exploded perspective component view of an earbud and sound processor according to embodiments of the present disclosure.
Figure 6:
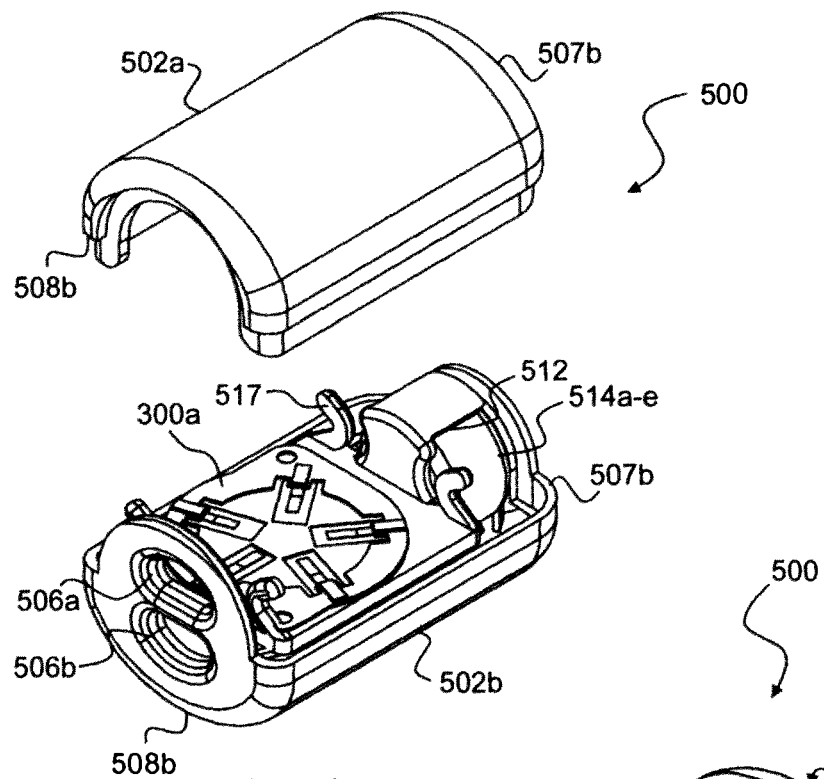
FIG. 6 is a part-exploded perspective view of the earbud and sound processor shown in FIG. 5.
Figure 7:
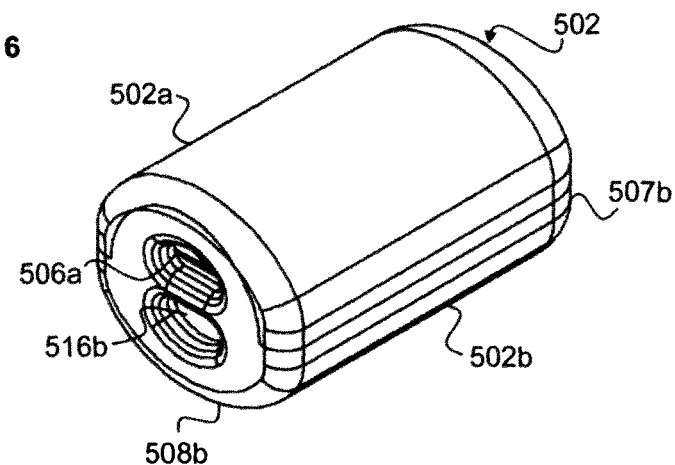
FIG. 7 is a perspective assembled view of the earbud and sound processor shown in FIG. 5.

A sound processor 500 according to embodiments of the present disclosure is shown in FIGS. 5 to 7. The sound processor 500 may be used as the sound processor 100 in the system 10 of FIG. 1. The sound processor 500 is an in-ear mechanical sound processor. FIG. 5 shows an exploded view of the sound processor 500. FIG. 6 shows the mechanical sound processor 500 partly assembled with part of the enclosure removed. FIG. 7 shows the sound processor 500 in assembled form.

The sound processor 500 comprises an acoustic enclosure 502 shaped and configured to be inserted into an ear canal of a human. The acoustic enclosure 502, also referred to herein as an earbud enclosure, comprises a cylindrical body having a distal end 507 and a proximal end 508, the enclosure 502 shaped to conform to the ear canal. In this embodiment, the acoustic enclosure 502 has an oval cross-section. An oval cross-section may better conform to the human ear canal thereby increasing the overall size of the bud (and thus internal volume for resonators, processing means, and other hardware) without impacting comfort or injury to a user. The acoustic enclosure 502 is configured to be inserted, in use, by its distal end 507 into an ear canal. The distal and proximal ends 507, 508 of the acoustic enclosure 502 are thus preferably each provided with contoured edges to enable insertion and removal of the sound processor 500 into and out of an ear canal without risk of irritation or injury.

The acoustic enclosure 502 may be formed of first and second enclosure portions 502a, 502b configured to enclose all other elements of the mechanical sound processor 500, as shown in FIGS. 5 to 7. In such embodiments, the first and second enclosure portions 502a, 502b may each comprise coupling elements configured to mutually engage to form the acoustic enclosure 502. In other embodiments, the first and second enclosure portions 502a, 502b may be manufactured as a single piece.

The acoustic enclosure 502 may be provided with acoustic ports 506a, 506b configured to allow the passage of sound pressure waves into the acoustic enclosure 502 from the proximal end 508 of the acoustic enclosure 502 which, when the sound processor 500 is inserted into an ear canal, is facing the outside of the ear. In addition, the acoustic enclosure 502 may comprise an acoustic port 509 at the distal end 507 of the acoustic enclosure 502 configured to allow air to travel through the sound processor 500 between the proximal end 508 and the distal end 507. Providing the additional port 509 at the proximal end 508 of the sound processor 500 reduces the build-up of pressure within the acoustic enclosure 502, thereby improving the flow of sound pressure over the first and second acoustic devices 300a, 300b.

The sound processor 500 further comprises a frame 505, for supporting first and second acoustic devices 300a, 300b within the acoustic enclosure 502. The first and second acoustic device 300a, 300b may be similar to the acoustic device 300 described with reference to FIGS. 2 to 4 or may be replaced with the conventional microphone 700 described herein. The acoustic devices 300a, 300b may be spaced axially apart, their front planar surfaces facing a rotational axis of the acoustic enclosure 502. In some embodiments, the front planar surface of the acoustic devices 300a, 300b are positioned so as to face one another such that the axis of their planar surfaces of each device 300a, 300b is substantially parallel to the axis of the cylindrical body of the acoustic enclosure 502. In other embodiments, the acoustic devices 300a, 300b may be distributed longitudinally relative to the rotational axis of the acoustic enclosure 502. In other embodiments, the acoustic devices 300a, 300b may be angled relative to the rotational axis of the acoustic enclosure 502.

The first and second acoustic devices 300a, 300b may be provided with respective mating portions 513a, 513b configured to co-locate with mating portions 515 of on the frame 505 so as to secure the position of the first and second acoustic device 300a, 300b relative to the frame 505. The frame 505 may further comprise stabilising members 517 configured to engage with internal walls of the first and second enclosure portions 502a, 502b when the first and second enclosure portions 502a, 502b are brought together in a mating configuration. In doing so, the stabilising members 517 prevent the frame from moving relative to the enclosure portions 502a, 502b when the mechanical sound processor 500 is fully assembled.

The in-ear acoustic enclosure 502 may be configured to enclose one or more of sensing electronics 511 (seen in FIG. 8) for sensing and processing electrical signals received from the acoustic devices 300a, 300b, a battery housing 510 for housing one or more batteries, one or more batteries 512 (if provided), and at least one interface in the form of a transmission coil 514 for wirelessly transmitting signals processed by the sensing electronics 511 to devices external to the mechanical sound processor 500. In the embodiment shown, a plurality of transmission coils 514a-514e is provided for wirelessly transmitting electrical signals output by the electrodes 314a-314e of the plurality of beam resonators 306 across separate transcutaneous communication links or channels. In another embodiment, the sensing electronics 511 may encode the individual electrical signals into a single channel for transmission at a single further transmission coil 514f across a combined transcutaneous communication link. The transmission coils 514a-514e, 514f may be positioned next to or integrated with the one or more batteries 512 so as to enable the transmission coils 514a-514e, 514f to inductively couple to external coils using near field magnetic induction (NFMI) or the like. In some embodiments the transmission coils 514a-e, 514f of the sound processor 500 are positioned in a linear array proximate a length of the acoustic enclosure 502, as shown schematically in the system diagram of FIGS. 1 and 8, so as to be arranged in close proximity to the tissue of the ear canal when inserted into the ear canal. In some embodiments in which the in-ear sound processor 500 is to be mounted on or behind the ear, the transmission coils 514a-e and 514f may be located in a separate transmitter enclosure (not shown) externally of the acoustic enclosure 502. In this case, the separate transmitter enclosure housing the transmission coils 514a-514e, 514f may be inserted into the ear canal. A wire (not shown) may connect the sensing electronics 511 in the sound processor 500 to the externally located transmission coils 514a-e, 514f.

In some embodiments, the enclosure 502 may comprise one or more keying features configured to engage with one or more features of an ear to locate the wireless transmitters 514a-e, 514f in a predetermined orientation relative to the ear when the in-ear mechanical sound processor 500 is inserted into the ear or when the separate enclosure housing the transmission coils 514a-4, 514f is inserted into the ear. Such keying features can be accomplished by a patient specific overmould that conforms to the pinna and ear canal shape of the individual. Other retention features may be employed such as replaceable grommets that hold the enclosure 502 in the ear canal, providing a location and retention feature. This alignment assures correct coupling to the implanted receive coils 604a-e, 604f, 604g, to maximise efficiency and robust communication transfer.

The resonators 306 of the acoustic devices 300a, 300b may be tuned so as to have differing natural frequencies and therefore maximum displacements at different frequencies of incident sound pressure waves. For example, the first acoustic device 300a may be configured for low frequency operation and the second acoustic device 300b may be configured for high frequency operation. In some embodiments, the first acoustic device 300a may have a frequency response covering frequencies up to 2000 Hz and the second acoustic device 300b may have a frequency response covering 2000 Hz-8000 Hz such that the combined frequency response of the acoustic device 300a, 300b covers a larger combined frequency range, e.g. 200 Hz to 8000 Hz or the frequency range of human speech. By providing two acoustic devices 300a, 300b spaced axially and opposite one another in the acoustic enclosure 502, a larger frequency range can be covered with more granularity (e.g. 10 channels) whilst maintaining the small form-factor required for the sound processor 500.

The piezoelectric resonators 306, cavity/cavities 304, diaphragm/membrane 302 and electrodes 314 may be formed by additive manufacturing (or three-dimensional (3D) printing). The additive manufacturing may, for example, comprise projection micro stereolithography (or stereo-lithographic printing (SLP) or digital light processing (DLP)). Suitable projection micro stereolithography techniques and materials are described in 3D Optical Printing of Piezoelectric Nanoparticle-Polymer Composite Materials, ACS Nano 8(10), July 2014.

In alternative embodiments of the acoustic device, the plurality of resonators may comprise strain gauge resonators or capacitive resonators in place of piezo-electric resonators.

Figure 8:
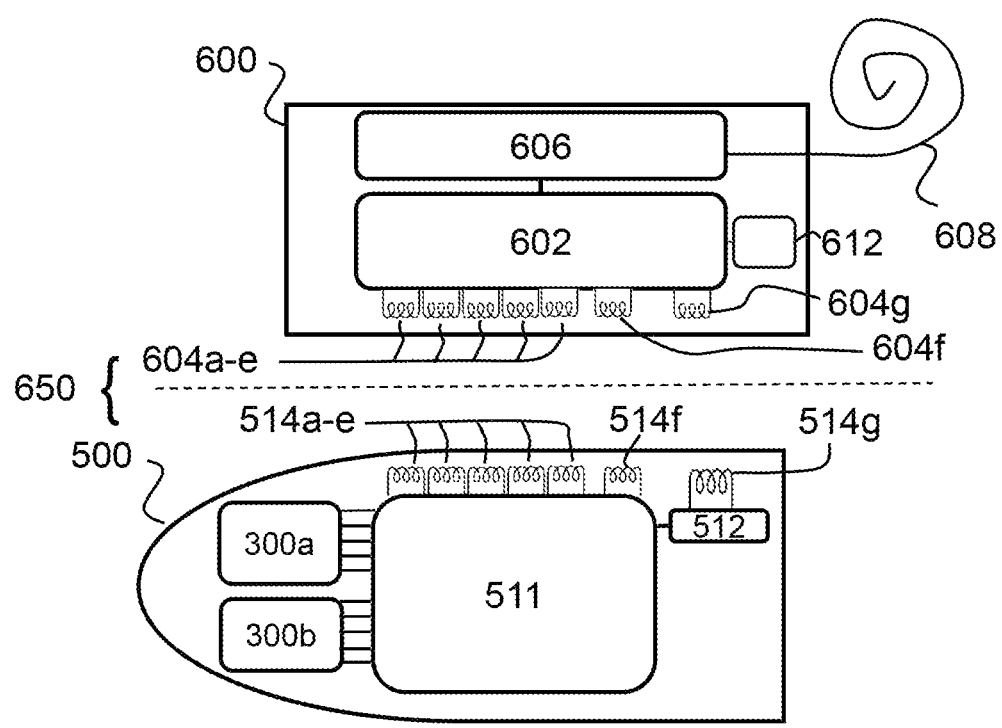
FIG. 8 is a schematic diagram of an earbud enclosing the sound processor and wireless communication links according to an embodiment of the disclosure and the cochlear implant shown in FIG. 1.
Figure 9:
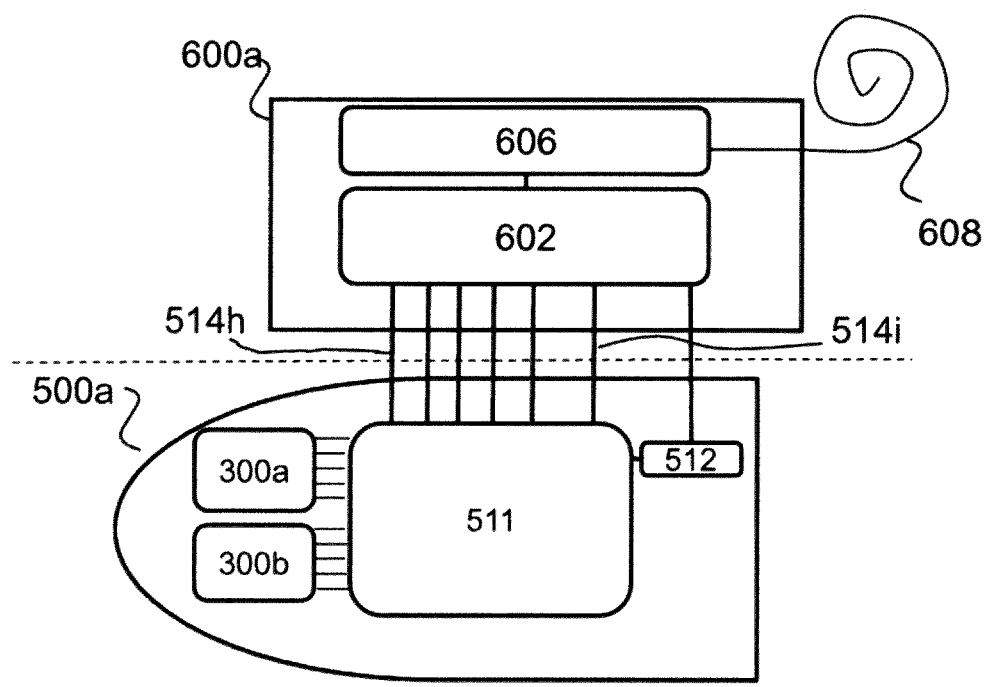
FIG. 9 is a schematic diagram of an earbud enclosing the sound processor and wired communication links according to an embodiment of the disclosure and the cochlear implant shown in FIG. 1.

As mentioned with regard to FIG. 1 above, the sound processors 100, 500 described above may be configured for use with cochlear implants, for example the cochlear implant 600 of FIG. 1. For example, the sound processor 500 may be configured to transmit, wirelessly or by wire, electrical signals relating to beam displacement, resonance, movement and oscillation to the cochlear implant 600. By way of example, FIGS. 1 and 8 show the sound processor 500 coupled to a cochlear implant 600 wirelessly. FIG. 9 shows a variation of the sound processor 500a coupled to a cochlear implant 600a by wire.

With reference to the anatomic representation of FIG. 1, FIG. 8 is a schematic diagram of the coupling of the sound processor 500 and the cochlear implant 600 when the sound processor 500 is inserted into the ear canal. Electrically active parts of the sound processor 500 including the first and second acoustic devices 300a, 300b, the sensing electronics 511, the transmission coils 514a to 514e, 514f and battery 512, are illustrated. In the present embodiment, the first acoustic device 300a is configured for low frequency operation and the second acoustic device 300b is configured for high frequency operation. The first acoustic device 300a outputs five low frequency electrical signals that are transmitted over five separate transcutaneous communication links 650 via transmission coils 514a-514e. The second acoustic device 300b outputs five high frequency electrical signals that are encoded at the sensing electronics 511 for transmission over a single channel via transmission coil 514f. In addition, a further separate transmission coil 514g is provided for transmission of electrical power, either from the battery 512 as shown in FIG. 8 or from an external battery 712, seen in FIG. 12.

The cochlear implant 600 comprises a receiver 602 comprising a plurality of radio-frequency (RF) coils 604a-g, a stimulator 606 and an electrode array 608 for stimulating the cochlear nerve (not shown). The electrode array 608 has a plurality of electrodes, each electrode configured to stimulate a neuron of the cochlea. The receiver 602 is configured to receive, over separate transcutaneous communication links 650, a plurality of electrical signals output by the transmission coils 514a to 514f and the transmission coil 514g of the sound processor 500. As shown in FIG. 8, the receiver 602 is configured for transcutaneous power and data transfer to the processor 606 via the RF coils 604a-g. The sensing electronics 511 of the sound processor 500 are configured to transmit via the RF coils 514a to 514f stimulation data pertaining to the acoustic devices 300a, 300b to the stimulator 606 via the receiver 602. The stimulator 606 is configured to apply the stimulation data received by the receiver 602 to the electrodes of the electrode array 608 to stimulate the neurons of the cochlea. The implant 600 may be powered by an internal power source 612, for example a rechargeable battery or capacitor, which can be recharged either from the battery 512 of the sound processor 500 or from an external battery or power source 712, seen in FIG. 12, via the transmission coil 514g and a separate wireless inductive coil 604g in the receiver 602.

FIG. 9 shows an embodiment of a sound processor 500a which is a further variation of the sound processor 500 shown in FIG. 8 and a cochlear implant 600a which is a variation of the cochlear implant 600 shown in FIG. 8. Like parts have been given like numbering. In this variation, the sound processor 500a is connected to the cochlear implant 600a by one or more wires 514h over which data and/or power can be delivered to the cochlear implant 600a from the sound processor 500a. In the embodiment shown, the acoustic device 300 outputs five low frequency electrical signals that are transmitted over five separate transcutaneous wired links 514h. A further five high frequency electrical signals are output from the acoustic device 300b and are transmitted over a further separate transcutaneous wired link 514i. In some embodiments, the one or more wires 514h, 514i may be interconnected by a percutaneous plug (not shown) of the cochlear implant 600a.

FIG. 10 shows an embodiment of a sound processor 500b which is a further variation of the mechanical sound processor 500 shown in FIG. 8 and the cochlear implant 600 shown in FIG. 8. Like parts have been given like numbering. In this variation, the sound processor 500b includes a conventional microphone 700 in place of the acoustic devices 300a, 300b. The microphone 700 outputs a broadband frequency response signal that is band pass filtered into five low frequency electrical signals that are transmitted over five separate transcutaneous communication links 650 via transmission coils 514a-514e and five high frequency electrical signals that are encoded at the sensing electronics 511 for transmission over a single channel via transmission coil 514f. In addition, a further separate transmission coil 514g is provided for transmission of electrical power, either from the battery 512 as shown in FIG. 8 or from an external battery 712, seen in FIG. 12.

FIG. 11 shows an embodiment of a sound processor 500c which is the same as the sound processor 500b shown in FIG. 10 and the cochlear implant 600a shown in FIG. 9. Like parts have been given like numbering. In this variation, the sound processor 500c includes a conventional microphone 700 and is connected to the cochlear implant 600a by one or more wires 514h over which data and/or power can be delivered to the cochlear implant 600a from the sound processor 500c. In the embodiment shown, the microphone 700 outputs a broadband frequency response signal that is band pass filtered into five low frequency electrical signals that are transmitted over five separate transcutaneous wired links 514h. A further five high frequency electrical signals are transmitted over a further separate transcutaneous wired link 514i. In some embodiments, the one or more wires 514h, 514i may be interconnected by a percutaneous plug (not shown) of the cochlear implant 600a.

Figure 12:
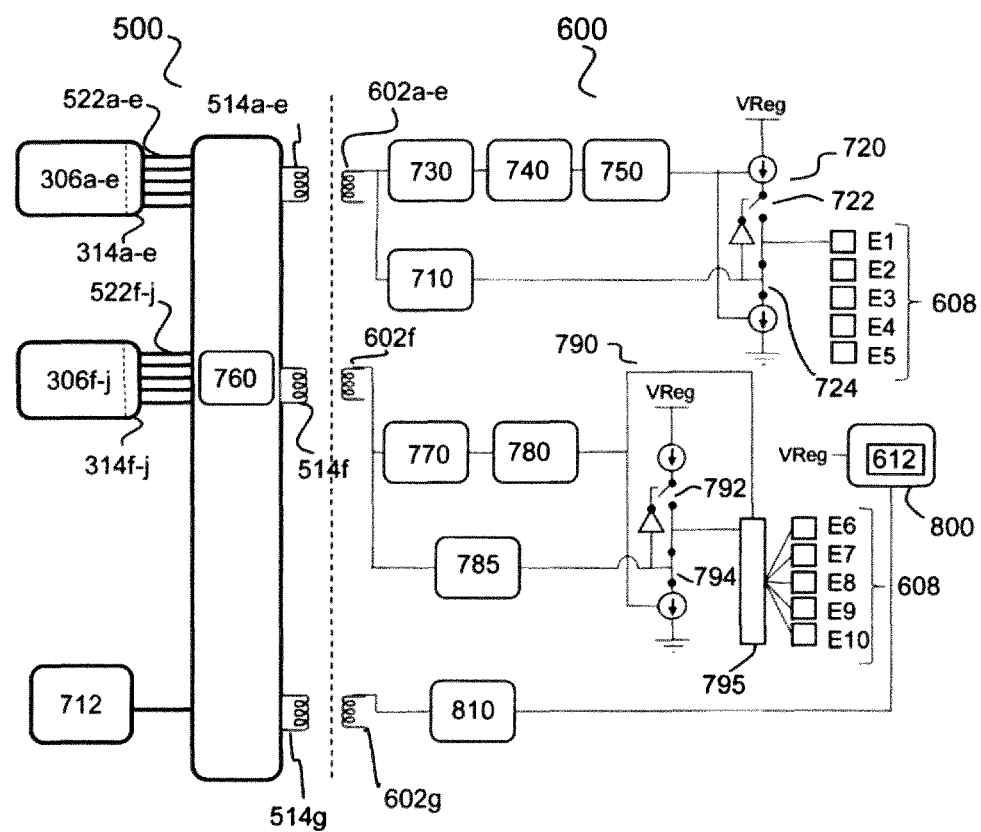
FIG. 12 is a schematic representation of an implementation architecture of a system including the sound processor and the cochlear implant of FIG. 8.

FIG. 12 shows a schematic diagram of the coupling of a sound processor 500 via the inductive coils 514a-g with corresponding receiving coils 602a-g of the implant 600, together with an embodiment of the processing electronics used to process the electrical signals transmitted from resonators 306a-j of the sound processor 500 to provide a stimulation current to the electrodes of the electrode array 608.

As shown in the diagram of FIG. 12, the plurality of resonators 306a-306j is divided into a first resonator bank, for example of an acoustic device 300a, and a second resonator bank, for example of a second acoustic device 300b. Specifically, five low frequency resonators 306a-306e are banked together in the first resonator bank, the electrical output of which is to electrodes 314a-314e. In this embodiment, the resonant natural frequency of each of the five resonators 306a-306e is tuned to a frequency between 100 Hz and 1200 Hz. Each resonator electrical signal output has an independent communication link 650 to the implant 600 to convey frequency and amplitude data. The electrodes 314a-314e of the first resonator bank are coupled to sensing electronics 511 as may be required, for example to filter noise from the low frequency information in the electrical signals prior to transmission at the coils 514a-514e. The high frequency resonators 306f-306j are banked together in a second resonator bank, the electrical output of which is to electrodes 314f-314j. In this embodiment, the resonant natural frequency of each of the five resonators 306f-306j is tuned to a frequency between 1210 Hz and 6500 Hz. The frequency and amplitude data output of these resonators is communicated over a single channel via the coil 514f. It will be appreciated that in other embodiments, the low frequency resonators may extend up to a frequency of up to 2000 Hz, and the high frequency resonators would accordingly start at e.g. 2010 Hz, extending up to 6500 Hz or 8000 Hz.

In some embodiments, one or more of the transmission coils 514a-514e is tuned to a natural frequency of an electrical signal output by a respective electrical signal of output to which they are coupled. As these natural frequencies are adjacent to each other and the physical spacing of the coils 514a-514e is very close, coupling which is maximised across the transcutaneous link is then problematic for coupling on adjacent channels. Thus cross-talk may impact the transfer of the electrical signals at their respective natural frequencies. Therefore at least one of the transmission coils 514a-514e may be tuned to a higher frequency carrier signal selected to move the natural frequency out-of-band, typically by 1 decade (factor of 10) or more, of the adjacent coils to reduce the coupling effect and cross-talk across the individual transcutaneous communication links. For example, if the natural frequencies of two adjacent coils are 800 Hz and 1000 Hz respectively, the higher frequency carrier signal for the 1000 Hz coil may be tuned to be 1 decade higher e.g. 10000 Hz. This may be carried out on the plurality of communications links as required to keep all wireless transcutaneous communication links separated electrically from each other. In this arrangement, the electrical signal is transmitted at the carrier frequency to avoid interference during transmission with the transmission of another of the electrical signals. The natural frequency of each of the plurality of electrical signals is then filtered from the carrier frequencies in the implant receiver 602.

Accordingly, separate inductive communication links 650 are used to transmit the low frequency electrical signals from the electrical signal output of the first resonator bank. A further separate inductive link 650 is used to transmit the high frequency electrical signals from the electrical signal output of the second resonator bank of the sound processor 500. Electrical power from the external battery 712 is provided over a yet further separate inductive link 650 via transmission coil 514g and receiver coil 602g to power the electrode stimulation at the electrode array 608 of the implant 600. At the implant 600, the low frequency electrical signals are processed separately to the high frequency electrical signals to create the desired electrode stimulation currents on the plurality of electrodes, as will now be described.

The electrical signal output from each of the five inductive coils 514a-514e is transmitted over a separate inductive coil link 650 to a corresponding one of the five inductive coils 604a-604e at the receiver 602 of the implant 600.

Once received at the respective inductive coil 602, the stimulation current is generated directly from the electrical signals 522a-e without further signal processing. FIG. 12 illustrates a stimulation current circuit for creating a stimulation current from an acoustic device electrical signal 522a output for an electrode E1 of the electrode array 608. The electrical signal 522a from the acoustic device 306a is in the form of a sinusoidal voltage output. The circuitry to create the stimulation current at the electrode E1 consists of two main circuits. Firstly, the timing of the application of the stimulation current to the electrode E1 is driven by the extracted sinusoidal voltage signal as an input into a timing extractor 710. The timing extractor 710 may consist of a zero crossing detector circuit. The timing information output by the timing extractor 710 is provided directly to the E1 electrode switch via a switch control circuit 720. The switch control circuit 720 is a switching circuit having a first switch 722 and a second switch 724, one for each phase of the bi-phasic pulse of the electrical signal 522a. The timing information determines when to open and close the switches 722, 724 to stimulate the electrode E1. Biphasic pulses are used as a way to ensure charge balanced stimulation. Secondly, the envelope of the electrical signal 522a is extracted by an envelope detector 730 to provide the amplitude of the stimulation current, based on the loudness of the sound presented to the acoustic device 306a. The extracted amplitude is then processed through a programmable control module 740 to ensure it is within safety limits and also within a detectable range for the cochlear implant recipient. The control module 740 can be programmed to increase and decrease the sound level of the stimulation current based on requirements for a particular recipient of the implant. For example, each individual recipient has a maximum tolerable current amplitude and a minimum detectable current amplitude, measured during an initial calibration of the implant for the individual and within which band the current amplitude must remain for safe usage. The individual mapping information can be programmed into one or more registers and/or look-up tables that can be consulted by the control module 740 to allow for amplitude modification based on the loudness growth curve of the individual recipient.

The modified amplitude information output by the control module 740 controls the stimulation current via a voltage controlled current source (VCCS) 750. The VCCS 750 takes a small current as an input to operate a switch to output a higher current. Accordingly, the VCCS 750 can be used to boost the input current, which may be of the order of tens of µA, to a sufficient threshold level for stimulating the electrode E1, for example at least hundreds of µA up to 2 mA output current. An advantage of using a VCCS 750 for this purpose is that it can be controlled or tuned to provide a required output level based on the input voltage. Other methods of achieving a signal boost include a charge pump or a voltage doubler (not shown). Whilst these topologies can be used in place of the VCCS 750, their output is limited and does not provide the same ability to control the output current to a desired threshold level. The VCCS 750 outputs current directly into the switch control circuit 720. The switch control circuit 720 includes first and second current sources and an inverter that switches between the positive phase and negative phase of the bi-phasic pulse train to open and close the switches 722, 724 to stimulate the electrode E1. The above E1 channel circuitry is replicated for processing each of the electrical signals 522a-e received at the coils 602a-602e, for creating a stimulation current at a corresponding electrode E1-E5 of the electrode array.

The stimulation currents provided at the low frequency electrodes E1 to E5 of the electrode array 608 provide a phase-locked sound signal to the low frequency cochlea neurons. The system ensures as close to possible as direct stimulation from the sound signal into the auditory system. Delays are minimised due to reduced latency of data transmission from the sound processor 500 to the implant 600 and little to no information is discarded, in particular the TFS information that is so important to temporal and location cues. The multi-coil transmitter and receiver system for transmission of the low frequency electrical signals to the implant 600 and the replication of the stimulation current circuitry for each of the low frequency electrodes E1 to E5 allows each low frequency channel to stimulate either simultaneously or sequentially. This simultaneous or sequential stimulation of the low frequency electrodes E1 to E5 can be constant and/or sub-threshold (i.e. below what is perceptible or audible to the recipient) to provide temporal queues to aid the neural responses from higher frequency information and speech recognition.

Above frequencies of around 1.2 kHz, the ability to phase lock with the auditory nerves is diminished. Accordingly, the electrical signal output of the higher frequency electrodes 314f-314j are processed separately to the signal output of the electrodes 314a-314e. The electrodes 314f-314j are also coupled to the sensing electronics 511 (FIGS. 8-11) which, in addition to any required noise filtering, includes an encoder 760. The encoder 760 encodes the output from each of the electrical sources 314f-314j into a single further channel communication interface at an inductive coil 514f. Accordingly, the encoded communication has the benefit of reducing the size and power requirement of the inductive link and its associated electronics. The electrical signal transmitted from the inductive coil 514f is transmitted to a corresponding inductive coil 602f at the receiver 602 of the implant 600.

The transmitted data is then decoded into timing information at a pulse generator 785 according to the electrode to be stimulated, and the amplitude of the current pulse is extracted at a decoder 770. The stimulation rate for these high frequency channels can be based on the extracted fundamental frequency of the sound source, or an arbitrary pulse rate based on the physiological requirements of the recipient. The extracted amplitude is then processed through a programmable control module 780 to ensure it is within safety limits and also within an individually detectable range. The control module 780 can be programmed to increase and decrease the sound level of the stimulation current based on requirements for a particular recipient of the implant. As with the low frequency electrical signals, the high frequency timing and amplitude information is output directly into a switch control circuit 790. The switch control circuit 790 is essentially a multiplexer comprising of first and second current sources and an inverter that switches between the positive phase and negative phase of the bi-phasic pulse train to open and close a first switch 792 and a second switch 794 to provide an output to a switching bank 795. The switching bank 795 stimulates the corresponding electrode E6 to E10 that is chosen based on the tonotopic location of the electrode array for the recipient. Accordingly, the electrodes E6 to E10 are stimulated sequentially.

Power transmission to the implant 600 for the electrode stimulation is decoupled from the data transmission so that a more efficient and dedicated link can keep the internal power source 612 of the implant 600 charged up. Accordingly, the implant power source 612 is charged over a separate inductive link to the electrical data signals 522. The internal power source 612 may be part of a power management block 800 and may comprise a rechargeable battery or a capacitor storage cell. The internal power source 612 can be recharged from the external battery 712, via the inductive link comprising a transmitter coil 514g at the sound processor 500 and a receiver coil 602g at the implant receiver 602. The external battery 712 may be the same battery as the battery 512 of the mechanical sound processor 500 described above. In this case, the internal power source 612 can be continually charged whilst the sound processor 500 is in wireless (or wired) contact with the receiver coil 602g of the implant 600. Alternatively, the external battery 712 may be a separate battery associated with an external charger (not shown) for a faster recharge of the internal power source 612. In this case, a transmitter coil 514g may also be present in the external charger.

A rectifier 810 converts the AC current output at the coil 604g to a DC current output which is then provided directly to the internal power source 612. As seen in FIG. 12, the electrical power is connected to each of the switching circuits 720, 790 to provide power for the electrode stimulation. Where the internal power source 612 is a battery, the power link would be required to operate only when the battery is being recharged, for example once daily. However, where the internal power source 612 is a capacitor storage cell, the battery 512 of the mechanical sound processor 500 may continuously supply power to the implant 600 when it is in use and stimulating the electrode array from the sound information that is sent across the dedicated data interfaces 514a-e, 514f.

It will be apparent to the skilled person that whilst the embodiment of FIG. 12 relates to the sound processor 500, the processing electronics at the implant 600 following receipt of the electrical signals at the receiver 602 may be used with any of the sound processors 500, 500a, 500b, 500c described herein.

The sound processors, systems and medical implants of the present disclosure provide for a direct stimulation of the electrode array from sound waves received at the sound processors. Data transmission from the sound processor to the implant is separated from power transmission. The data transmission itself is also separated according to tuned audio frequency bands, where low frequency audio data signals are transmitted simultaneously or sequentially over a plurality of communication interfaces, and separately to the transmission of high frequency audio data signals. Accordingly, the result is a reduced requirement for signal processing, reduced delay in transmission of data, improved power transmission and little to no removal of TFS information. Stimulation rates for the low frequency audio data are phase-locked with the response of the neuron tuned to the respective frequency, therefore the system provides as near as possible a direct stimulation from the sound signal containing the TFS information into the auditory cortex, restoring the timing information that is critical to the understanding of pitch, and the location of speech, particularly in noisy environments.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A sound processor comprising:
   a communications arrangement configured to transmit each electrical signal of a plurality of electrical signals, respectively, across a plurality of separate transcutaneous communication links to a receiver-stimulator of a cochlear implant, wherein the plurality of electrical signals is generated in response to sound incident at the sound processor,
   a plurality of resonators, wherein each resonator of the plurality of resonators is electrically coupled to a respective electrode of a plurality of electrodes and the plurality of electrodes are respectively configured to output the plurality of electrical signals.

2. The sound processor of claim 1, further comprising an electrical signal output configured to generate the plurality of electrical signals in specific tuned audio frequency bands in respective audio channels, in response to sound incident at the sound processor in the specific tuned audio frequency bands, and further comprising a transmitter coupled to the electrical signal output for transmission of the plurality of electrical signals, wherein the transmitter is configured to transmit each electrical signal of the plurality of electrical signals across the plurality of separate transcutaneous communication links.

3. The sound processor of claim 2, wherein the transmitter comprises a plurality of interfaces, wherein each interface of the plurality of interfaces is coupled to the electrical signal output and is configured to transmit a respective one of the plurality of electrical signals over a respective one of the plurality of separate transcutaneous communication links.

4. The sound processor of claim 3, wherein the plurality of interfaces each comprise a wire.

5. The sound processor of claim 3, wherein the plurality of interfaces are wireless interfaces.

6. The sound processor of claim 5, wherein each wireless interface comprises an inductive coil.

7. The sound processor of claim 2, wherein the electrical signal output comprises the plurality of electrodes.

8. The sound processor of claim 1, wherein each electrical signal of the plurality of electrical signals is output at the electrodes in response to sound incident at respective resonators of the plurality of resonators, at least some of the plurality of resonators having a different resonant frequency from each other.

9. The sound processor of claim 1, wherein the communications arrangement is configured to transmit each electrical signal of the plurality of electrical signals simultaneously across the plurality of separate transcutaneous communication links to the receiver-stimulator.

10. A system comprising:
    (a) the sound processor of claim 1; and
    (b) an implant comprising:
       (i) a plurality of implant electrodes, each implant electrode configured to stimulate the cochlea,
       (ii) a receiver-stimulator configured to receive, over the plurality of separate transcutaneous communication links, each of the electrical signals transmitted from the transmitter of the sound processor, and apply each of the electrical signals to a respective one of the plurality of implant electrodes.

11. The system of claim 10, wherein the transmitter is a wireless transmitter and the receiver-stimulator is a wireless receiver-stimulator.

12. The system of claim 10, wherein the implant further comprises a power source.

13. The system of claim 12, wherein the power source is rechargeable via the receiver-stimulator over a separate wireless or wired link.

14. The system of claim 10, wherein the implant is powered by an external power source via a separate wireless or wired link.

15. The system of claim 10, wherein the sound processor comprises an electrical signal output configured to generate the plurality of electrical signals in specific tuned audio frequency bands in respective audio channels, in response to sound incident at the sound processor in the specific tuned audio frequency bands, and further comprising a transmitter coupled to the electrical signal output for transmission of the plurality of electrical signals, wherein the transmitter is configured to transmit each electrical signal of the plurality of electrical signals across the plurality of separate transcutaneous communication links.

16. The system of claim 15, wherein the transmitter comprises a plurality of interfaces, wherein each interface of the plurality of interfaces is coupled to the electrical signal output and is configured to transmit a respective one of the plurality of electrical signals over a respective one of the plurality of separate transcutaneous communication link.

17. The system of claim 16, wherein the plurality of interfaces each comprise a wire.

18. The system of claim 16, wherein the plurality of interfaces are wireless interfaces.

19. The system of claim 18, wherein each wireless interface comprises an inductive coil.

20. The system of claim 15, wherein the electrical signal output comprises the plurality of electrodes.

21. The system of claim 20, wherein each electrical signal of the plurality of electrical signals is generated at the electrodes in response to sound incident at respective resonators of the plurality of resonators, at least some of the plurality of resonators having a different natural frequency.

22. The system of claim 21, wherein the plurality of resonators are piezoelectric resonators or strain gauge resonators or capacitive cell resonators.

23. A sound processor comprising:
a communications arrangement configured to transmit each electrical signal of a plurality of electrical signals, respectively, across a plurality of separate transcutaneous communication links to a receiver-stimulator of a cochlear implant, wherein the plurality of electrical signals is generated in response to sound incident at the sound processor;
an electrical signal output configured to generate the plurality of electrical signals in specific tuned audio frequency bands in respective audio channels, in response to sound incident at the sound processor in the specific tuned audio frequency bands, and further comprising a transmitter coupled to the electrical signal output for transmission of the plurality of electrical signals, wherein the transmitter is configured to transmit each electrical signal of the plurality of electrical signals across the plurality of separate transcutaneous communication links, wherein the electrical signal output comprises a plurality of electrodes;
a plurality of resonators, each resonator of the plurality of resonators being coupled to a respective electrode of the plurality of electrodes, wherein each electrical signal of the plurality of electrical signals is generated at the electrodes in response to sound incident at respective resonators of the plurality of resonators, at least some of the plurality of resonators having a different natural frequency from each other.

24. The sound processor of claim 23, wherein the plurality of resonators are piezoelectric resonators or strain gauge resonators or capacitive cell resonators.

25. A system comprising:
(a) a sound processor comprising a communications arrangement configured to transmit each electrical signal of a plurality of electrical signals across separate transcutaneous communication links to a receiver-stimulator of a cochlear implant, wherein the plurality of electrical signals is generated in response to sound incident at the sound processor; and
(b) an implant comprising:
 (i) a plurality of implant electrodes, each implant electrode configured to stimulate the cochlea,
 (ii) a receiver-stimulator configured to receive, over separate transcutaneous communication links, each of the electrical signals transmitted from the transmitter of the sound processor, and apply each of the electrical signals to a respective one of the plurality of implant electrodes,
wherein the sound processor is enclosed in an earbud, and wherein the wireless receiver-stimulator is configured to align with the wireless transmitter when the implant is implanted near or adjacent an ear of a patient and the earbud is inserted into the ear.

* * * * *